United States Patent [19]

Geisen et al.

[11] Patent Number: 5,215,990

[45] Date of Patent: * Jun. 1, 1993

[54] SUBSTITUTED PYRIMIDINE DERIVATIVES, A PROCESS FOR THE PREPARATION THEREOF AND THE USE THEREOF AS REAGENTS

[75] Inventors: Karl Geisen, Frankfurt am Main; Roland Utz, Messel; Hildegard Nimmesgern, Frankfurt am Main; Hans-Jochen Lang, Hofheim am Taunus, all of Fed. Rep. of Germany

[73] Assignee: Hoechst Aktiengesellschaft, Frankfurt am Main, Fed. Rep. of Germany

[ * ] Notice: The portion of the term of this patent subsequent to Aug. 11, 2009 has been disclaimed.

[21] Appl. No.: 741,810

[22] Filed: Aug. 8, 1991

[30] Foreign Application Priority Data

Aug. 10, 1990 [DE] Fed. Rep. of Germany ....... 4025387

[51] Int. Cl.$^5$ ................. C07D 403/00; A61K 31/495; A01N 43/60
[52] U.S. Cl. ..................................... 514/255; 544/295
[58] Field of Search .................. 544/295, 386, 319; 514/255

[56] References Cited

U.S. PATENT DOCUMENTS

| | | | |
|---|---|---|---|
| 2,362,276 | 11/1944 | Jayne, Jr. | 544/386 |
| 2,973,362 | 2/1961 | Schorsch | 544/386 |
| 3,190,883 | 7/1965 | Geschickter et al. | 544/386 |
| 3,296,261 | 1/1967 | Partyka | 544/319 |

FOREIGN PATENT DOCUMENTS 0198583 10/1986 European Pat. Off. .
3905364 8/1990 Fed. Rep. of Germany .

OTHER PUBLICATIONS

P. J. Brown, "The Pyrimidines" (1962) pp. 31, 36, 50, 162–165, 186–188.

Primary Examiner—Mukund J. Shah
Assistant Examiner—Matthew V. Grambling
Attorney, Agent, or Firm—Finnegan, Henderson, Farabow, Garrett & Dunner

[57] ABSTRACT

Pyrimidine derivatives of the formula I

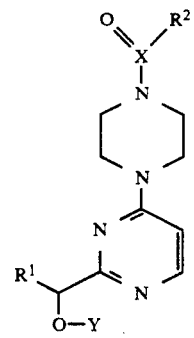

in which $R^1$, $R^2$, X and Y have the stated meaning, the salts thereof and a process for the preparation thereof are described. Because of their sorbitol-accumulating activity, they are suitable for use as reagents for an advantageous pharmacological screening model for testing aldose reductase inhibitors.

7 Claims, No Drawings

SUBSTITUTED PYRIMIDINE DERIVATIVES, A PROCESS FOR THE PREPARATION THEREOF AND THE USE THEREOF AS REAGENTS

DESCRIPTION

Elevated intracellular sorbitol concentrations occur in diabetic individuals (animal, human). There is increased production of sorbitol by the enzyme aldose reductase when blood glucose is elevated. Sorbitol accumulation can be prevented by aldose reductase inhibitors.

Screening for aldose reductase inhibitors (ARI) is carried out on streptozotocin-diabetic rats. 1 to 2 weeks after induction of diabetes with 60 mg of streptozotocin sulfate per kg of rat the animals are employed in ARI screening. The measure used for the efficacy of aldose reductase inhibitors is the reduction in the elevated sorbitol content in erythrocytes, in nerves and the lens 5-6 h after treatment with the ARIs to be investigated.

Streptozotocin is a carcinogen. Administration of streptozotocin and housing of the animals after administration (2-3 days) must therefore take place under biohazard conditions. The urine excreted during the first two days after streptozotocin administration must undergo special disposal, and the contaminated cages must undergo specific cleaning. However, streptozotocin not only has a carcinogenic and toxic effect on β cells of the pancreas, it also causes hepatic and renal damage. For this reason the animals are not employed in the ARI screening until 10-14 days after administration.

The use of pyrimidine derivatives of the formula I'

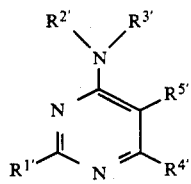

in which $R^1$, $R^{4'}$ and $R^{5'}$ are identical or different and are hydrogen, halogen, cyano, nitro, trifluoromethyl, $(C_1-C_6)$-alkyl, $(C_1-C_6)$-hydroxyalkyl-, $(C_1-C_6)$-alkoxy, $(C_6-C_{12})$-aryl or amino, and $R^{3'}$ are identical or different and are hydrogen, $(C_1-C_6)$-alkyl, $(C_6-C_{12})$-aryl or $(C_6-C_{12})$-aralkyl with 1-4 alkyl carbon atoms, or $R^{2'}$ and $R^{3'}$ form, together with the nitrogen to which they are bonded, the azetidino, pyrrolidino, piperidino, piperazino or morpholino group, or an azetidino, pyrrolidino, piperidino, piperazino or morpholino group which is substituted with identical or different groups $R^{6'}$ and $R^{7'}$, where $R^{6'}$ and $R^{7'}$ are $(C_1-C_6)$-alkyl, sulfamoyl, N-$(C_1-C_6)$-alkylsulfamoyl, N,N-$(C_1-C_4)$-dialkylsulfamoyl, $(C_1-C_6)$-alkoxycarbonyl, N,N-$(C_1-C_4)$-dialkylcarbamoyl, N-$(C_1-C_4)$-alkylcarbamoyl, N-$(C_6-C_{12})$-arylcarbamoyl, $(C_6-C_{12})$-arylcarbamoyl which is substituted in the aryl radical by $(C_1-C_4)$-alkyl, $(C_1-C_4)$-alkoxy, halogen, $NO_2$, $NH_2$, CN or $CF_3$, or carbamoyl, $(C_1-C_6)$-alkylcarbonyl, $(C_6-C_{12})$-arylcarbonyl, $(C_6-C_{12})$-arylcarbonyl which is substituted in the aryl radical by $(C_1-C_4)$-alkyl, $(C_1-C_4)$-alkoxy, halogen, $NO_2$, $NH_2$, CN or $CF_3$, or $(C_1-C_6)$-alkylsulfonyl, $(C_1-C_6)$-alkylsulfinyl, $(C_6-C_{12})$-arylsulfonyl, $(C_6-C_{12})$-arylsulfonyl which is substituted in the aryl radical by $(C_1-C_4)$-alkyl, $(C_1-C_4)$-alkoxy, halogen, $NO_2$, $NH_2$, CN or $CF_3$, or heteroarylcarbonyl or heteroarylsulfonyl, or one of the substituents $R^{6'}$ and $R^{7'}$ is hydrogen, and of the physiologically tolerated salts thereof as tool has already been proposed (cf. German Offenlegungsschrift 39 05 364 corresponding to EP-A 0 384 370 and U.S. patent application No. 07/482,053). According to the statements in this patent application, the compounds described therein cause, without influencing the blood glucose, on acute and chronic, oral or parenteral administration to normal, non-diabetic rats an intracellular increase in sorbitol which can be prevented by simultaneous treatment with aldose reductase inhibitors.

It has now been found, surprisingly, that the pyrimidine derivatives of the formula I

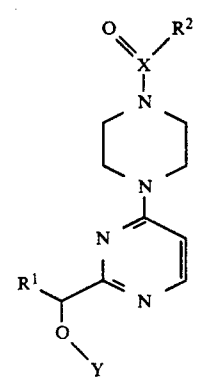

which are not specified expressis verbis in German Offenlegungsschrift 39 05 364, and the physiologically tolerated salts thereof, have considerably more beneficial properties. They cause, without influencing blood glucose, on acute and chronic, oral or parenteral administration, an intracellular increase in sorbitol. The increase in sorbitol induced by the pyrimidine derivatives of the formula I is prevented by simultaneous treatment with aldose reductase inhibitors. The sorbitol-accumulating pyrimidine derivatives of the formula I are therefore suitable for a novel, simplified, less costly and time-consuming acute screening for aldose reductase inhibitors on normal, non-diabetic rats. In contrast to the examples specified in the German patent application, the compounds of the above formula I show a sorbitol-accumulating effect in vivo not only on the rat but also on other species. A very considerable and unexpected advantage is that compounds of the formula I induce elevations in sorbitol not only in vivo but also in vitro, for example on erythrocytes, and thus an even lower cost and more easily implemented test model for, for example, aldose reductase inhibitors can be achieved.

The present invention therefore relates to pyrimidine derivatives of the formula I

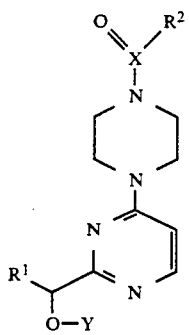

in which

R¹ is hydrogen or methyl,

R² is $C_1$-$C_6$-alkyl, $C_5$-$C_7$-cycloalkyl, unsubstituted phenyl, phenyl which is mono- or disubstituted by methyl, chlorine, fluorine, trifluoromethyl, methoxy, $CH_3$—$SO_n$ with n equal to zero, 1 or 2, or —$SO_2$—$NH_2$, where in the case of disubstitution the substituents are identical or different,

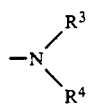

where R³ and R⁴ are identical or different and are hydrogen or $C_1$-$C_6$-alkyl, or is pyridyl or, if X is a carbon atom, is also hydrogen, X is a carbon atom or SO, and Y is a hydrogen, $C_1$-$C_6$-alkyl, benzyl, acetyl or benzoyl, and the physiologically tolerated salts thereof.

The alkyl radicals mentioned for Y and R² in the formula I can be straight-chain or branched.

Preferred pyrimidine derivatives of the formula I are those in which a)
R¹ is hydrogen,
R² is $C_1$-$C_3$-alkyl, unsubstituted phenyl or mono- or disubstituted phenyl, where the substituents have the stated meanings, and
X and Y have the stated meanings, b)
R¹ is hydrogen,
R² is

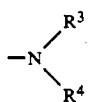

where R³ and R⁴ are identical or different and are methyl or ethyl,
X is SO, and
Y has the stated meaning, c)
R¹ is hydrogen,
R² is pyridyl,
X is a carbon atom, and
Y has the stated meaning,
and the physiologically tolerated salts thereof.

R¹, R² and X preferably have the meanings stated under a) to c), and Y is preferably a hydrogen atom.

A very particularly preferred pyrimidine derivative of the formula I is the one in which R¹ is hydrogen, R² is

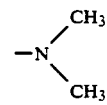

X is SO and Y is hydrogen, and the physiologically tolerated salts of this compound.

The invention furthermore relates to a process for the preparation of compounds of the formula I, which comprises, in a manner known per se, a) reacting a compound of the formula II

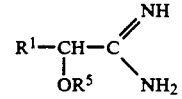

in which R¹ has the meaning stated for formula I, and R⁵ is a suitable ether protective group such as methyl or benzyl, or the acid addition salt thereof, with a compound of the formula III

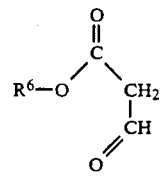

in which R⁶ is methyl or ethyl, or one of the alkali metal salts thereof, to give a compound of the formula IV

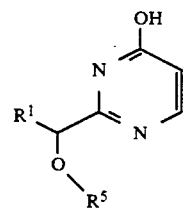

in which R¹ has the meanings stated for formula I and R⁵ has the meanings stated for formula II, converting a resulting compound of the formula IV with an inorganic acid chloride such as, for example, with phosphorus oxychloride into a pyrimidine derivative of the formula V

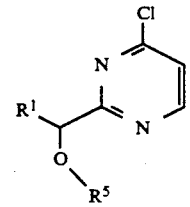

in which the radicals R¹ have the meanings stated for formula I and R⁵ has the meaning stated for formula II, and subsequently, α) reacting a resulting compound of the formula V with a piperazine derivative of the formula VI

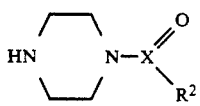

in which $R^2$ and X have the meanings stated for formula I, to give a compound of the formula VII

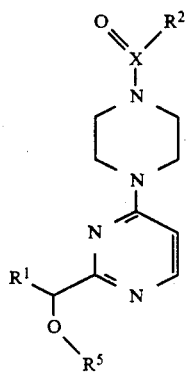

in which $R^1$, $R^2$ and X have the meanings stated for formula I and $R^5$ has the meaning stated for formula II, or β) converting a resulting compound of the formula V with unsubstituted piperazine into a compound of the formula VIII

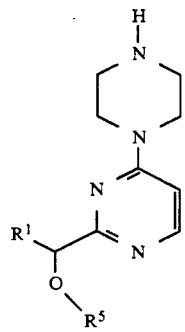

in which $R^1$ has the meaning stated for formula I and $R^5$ has the meaning stated for formula II, and converting the resulting compound VIII with an acid chloride of the formula IX

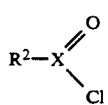

in which $R^2$ and X have the meanings stated for formula I, into a compound of the formula VII with the stated meanings of the substituents, and converting a compound of the formula VII obtained as in α) or β) where appropriate in a manner known per se by an ether-cleaving reagent, for example with $BBr_3$, trimethylsilyl iodide, or by catalytic hydrogenation, when $R^5$ has the meaning of benzyl, into a compound of the formula I, b) converting a compound of the formula X

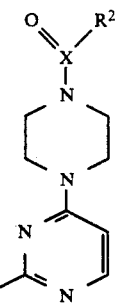

in which $R^1$, $R^2$ and X have the meanings stated for formula I, with a halogenating agent such as chlorine, bromine, N-bromosuccinimide, sulfuryl chloride or with trichloroisocyanuric acid, in a manner known per se into a compound of the formula XI

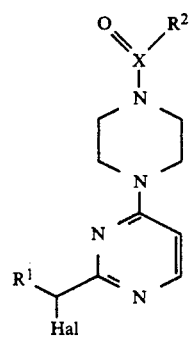

in which the substituents $R^1$, $R^2$ and X have the meanings stated for formula I, and Hal is Cl or Br, and converting a resulting compound of the formula XI either by direct hydrolysis or by reaction with an alkali metal salt of acetic or benzoic acid, for example sodium acetate or sodium benzoate, or the alkali metal salt of benzyl alcohol or the alkali metal salt of a $C_1$-$C_6$-alkyl alcohol into a compound of the formula I with $R^1$, $R^2$, X and Y having the stated meanings and, where appropriate, converting a compound of the formula I with Y not equal to hydrogen, obtained by process a) or b), in a manner known per se by acid or alkaline hydrolysis into a compound of the formula I with Y equal to hydrogen, where appropriate converting a resulting compound of the formula I with Y equal to hydrogen in a manner known per se into a compound of the formula I with Y equal to $C_1$-$C_6$-alkyl, benzyl, acetyl or benzoyl and, where appropriate, converting a resulting compound of the formula I into a physiologically tolerated salt.

If $R^5$ in compounds of the formula VII is methyl or benzyl, these compounds are final products of the formula I with Y equal to methyl or benzyl. These compounds are, where appropriate, subjected to the subsequent reactions.

Compounds of the formula VIII can also be obtained in a manner known per se by acid or alkaline hydrolysis of the compounds VII.

The conversion of compounds of the formula I with Y equal to hydrogen into those with Y not equal to hydrogen is carried out, for example, by direct acylation or by reaction with thionyl chloride via the compounds of the formula XI.

Process a) according to the invention is carried out in analogy to the processes described in the literature (cf., for example, D. J. Brown, The Chemistry of Heterocyclic Compounds, The Pyrimidines Suppl. I (1970), Suppl. II (1985), Wiley Interscience, N.Y. and literature cited therein).

The side-chain chlorination in process b) according to the invention is preferably carried out with trichloroisocyanuric acid in analogy to the statements by G. E. Jeromin et al., Side-Chain Chlorinations of N-Heterocycles with Trichloroisocyanuric Acid (TCC) in Chem. Ber. 120, 649–651 (1987).

Compounds of the formula I can be converted by reaction with acids into physiologically tolerated salts thereof.

To date it has been necessary to use diabetic animals to investigate compounds with an effect on late diabetic damage, for example aldose reductase inhibitors. It was necessary to provoke an artificial diabetic disorder in these animals by destroying the insulin-secreting β cells with toxic compounds such as streptozotocin, alloxan etc. The irreversibly damaged animals which—as described in the introduction—develop elevated blood glucose and intracellular sorbitol levels can, as a consequence of their diabetic disorder, be kept only with relatively elaborate and cost-intensive care measures and, because of their debilitation, can be kept free of secondary disorders, which in turn impair their utilizability, only with difficulty.

It was thus surprising that the compounds according to the invention, which are distinguished by being well tolerated, generate functional symptoms of the nature of diabetic neuropathy in healthy animals owing to intracellular polyol accumulation without preceding diabetic metabolic status.

Because of this ability of bringing about sorbitol accumulation, the compounds according to the invention are suitable in an advantageous manner as reagents for testing aldose reductase inhibitors in the pharmacological model on healthy animals. Furthermore, the compounds of the formula I are suitable as in vitro reagent for aldose reductase inhibitors. The invention therefore also relates to this use of the pyrimidine derivatives of the formula I and of the pharmacologically tolerated salts thereof.

The compounds according to the present invention, when administered orally in doses of 5–50 mg/kg of rat, caused a dose-dependent increase in the sorbitol concentration in the sciatic nerve and in the erythrocytes of normal and streptozotocin-diabetic rats within 4 to 5 hours.

After oral administration of 25 mg/kg of rat of the compound of Example 1 or 2, the sorbitol concentration reached in said tissues in the case of normal rats after 4–5 hours corresponds to that which streptozotocin-diabetic rats display after 8 days. The increase in sorbitol is prevented dose-dependently by simultaneous oral treatment with the ARI spiro-2,7-difluoro-9H-fluorene-9,4'-imidazolidine-2,5-dione (=HOE 843).

Apart from the compounds listed in the examples, the compounds of the formula I compiled in the following table, and the salts thereof, can be prepared.

Abbreviations used: methyl (Me), ethyl (Et), propyl (Prop), butyl (Bu), hexyl (Hex), acetyl (Ac), phenyl (Ph), benzoyl (Bz), iso (i) and cyclo (c).

TABLE

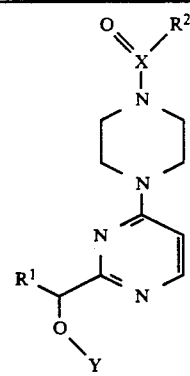

| $R^1$ | $R^2$ | X | Y |
|---|---|---|---|
| Me | $NMe_2$ | SO | H |
| Me | Ph | C | H |
| H | $NMe_2$ | SO | Ac |
| H | $NMe_2$ | SO | Bz |
| H | $NMe_2$ | SO | $Ph-CH_2$ |
| H | $NEt_2$ | SO | H |
| H | $NEt_2$ | SO | Me |
| H | $NEt_2$ | SO | Ac |
| H | $NBu_2$ | SO | H |
| H | $NH_2$ | SO | H |
| H | $NH_2$ | SO | Ac |
| H | Me | SO | H |
| H | Me | SO | Ac |
| H | Me | SO | Me |
| H | Et | SO | H |
| H | Prop | SO | H |
| H | iProp | SO | H |
| H | Ph | SO | H |
| H | —⟨Ph⟩—Me | SO | H |

TABLE

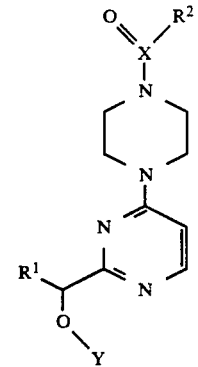

| $R^1$ | $R^2$ | X | Y |
|---|---|---|---|
| H | —⟨Ph⟩—Cl | SO | H |
| H | —⟨Ph⟩(Cl) | SO | H |

TABLE-continued

Structure (left side):
Piperazine with N-X(=O)-R² group on top N, and bottom N connected to pyrimidine bearing -CR¹H-O-Y at the 2-position.

| R¹ | R² | X | Y |
|---|---|---|---|
| H | 2-(CF₃)-phenyl | SO | H |
| H | 2-Cl-6-SO₂NH₂-phenyl | SO | H |
| H | 2,3-diCl-phenyl | SO | H |
| H | H | C | H |
| H | Me | C | H |
| H | Me | C | Me |
| H | Me | C | Ac |
| H | Prop | C | H |
| H | cHex | C | H |
| H | Ph | C | H |
| H | 4-Me-phenyl | C | H |
| H | 4-Cl-phenyl | C | H |
| H | 2-Cl-phenyl | C | H |
| H | 2,3-diCl-phenyl | C | H |

TABLE-continued

| R¹ | R² | X | Y |
|---|---|---|---|
| H | 2-Cl-5-SO₂Me-phenyl | C | H |
| H | 2-Cl-5-SO₂NH₂-phenyl | C | H |
| H | 4-OMe-phenyl | C | H |
| H | 3-pyridyl | C | H |

EXAMPLE 1

4-[4-(N,N-Dimethylsulfamoyl)piperzaino]-2-methylocymethylpyrimidine hydrochloride

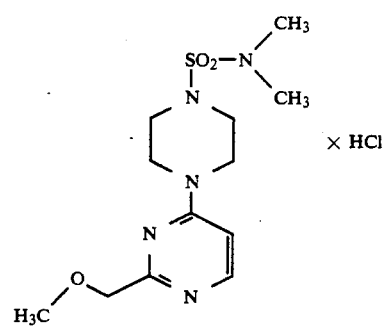

(a) 4-Hydroxy-2-methyloxymethylpyrimidine

Under an argon atmosphere, 31.5 g (0.72 mol) of sodium hydride are suspended in 690 ml of diisopropyl ether and, at room temperature, a mixture of 84.5 ml of ethylformate and 63.4 ml of ethyl acetate is added dropwise. The mixture is heated cautiously to 40°–44° C. After the vigorous evolution of hydrogen which starts during this, the mixture is stirred for a further 5 h with exclusion of moisture. The solid is filtered off with suction (96 g), the crude sodium salt of the formylacetic ester is dissolved in 350 ml of water, and 96 g (770 mmol) of methoxyacetamidine hydrochloride (cf. Chem. Abstr. 66, 37942×(1967)) dissolved in 350 ml of water are added. After the mixture has stood at room temperature for 3 days it is neutralized with hydrochloric acid, evaporated to dryness in vacuo and extracted by boiling several times with ethyl acetate. Evaporation of the solvent results in 62.5 g of product which is reacted further without further purification.

(b) 4-Chloro-2-methyloxymethylpyrimidine 47 g (335.7 mmol) of 4-hydroxy-2-methoxymethylpyrimidine (from stage a) are mixed with 210 ml of phosphorus oxychloride and stirred at 70° C. for 2 h and subsequently heated to boiling for 2.5 h. The excess phosphorus oxychloride is removed by distillation in vacuo, the residue is hydrolyzed with ice, and solid potassium bicarbonate is added to eliminate excess acid. Several extractions with methylene chloride are carried out, and the organic phase is evaporated in vacuo. The black residue is filtered through silica gel (n-heptane/ethyl acetate 1:1). 15.7 g of oil are obtained.

$^1$H NMR (60 MHz/DMSO): $\delta=8.82$ (d, J=5Hz, 1H); $\delta=7.67$ (d, J=5Hz, 1H); $\delta=4.57$ (s, 2H); $\delta=3.38$ (s, 1H)

(c)
4-[4-(N,N-Dimethylsulfamoyl)piperazino]-2-methyloxymethylpyrimidine hydrochloride 3.70 g (23.3 mmol) of 4-chloro-2-methyloxymethylpyrimidine (from stage b), 4.75 g (24.6 mmol) of N,N-dimethylsulfamoylpiperazine and 3.4 ml of triethylamine in 15.4 ml of dry tetrahydrofuran are heated to reflux for 7 hours. After the reaction mixture has been cooled to room temperature, the precipitated triethylammonium chloride is filtered off with suction and washed with ethyl acetate, and the filtrate is evaporated in vacuo. The remaining crude product is chromatographed on silica gel (ethyl acetate/methanol 9:1). 5.90 g of oily product are obtained.

$^1$H NMR (270 MHz/CDCl$_3$): $\delta=8.28$ (d, J=6Hz, 1H) $\delta=6.41$ (d, J=6Hz, 1H); $\delta=4.48$ (s, 2H); $\delta=3.75$ (t, J=5Hz, 4H); $\delta=3.33$(t, J=5Hz, 4H); $\delta=2.86$ (s, 6H)

To prepare the hydrochloride, 5.90 g of oil are dissolved in 25 ml of 2 normal ethanolic hydrochloric acid, and the solvent is evaporated off in vacuo. The residue is triturated with acetone, and the solid is filtered off with suction and dried at 40° C. under high vacuum.

4.1 g of hydrochloride of melting point 174–175° C. are obtained.

C$_{12}$H$_{22}$ClN$_5$O$_3$S (351.87) calc.: C 40.96 H 6.3 N 19.91. found: C 41.1 H 6.2 N 20.0.

EXAMPLE 2

4-[4-(N,N-Dimethylsulfamoyl)piperazino]-2-hydroxymethylpyrimidine

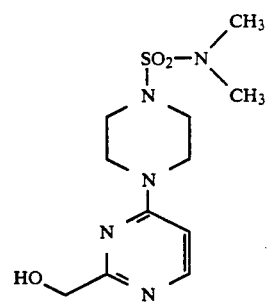

11.0 g (35 mmol) of 4-[4-(N,N-dimethylsulfamoyl)-piperazino]-2-methyloxymethylpyrimidine (Example 1) are dissolved in 45 ml of dry methylene chloride. Between 0° C. and +5° C., 13.2 g (52.5 mmol) of boron tribromide dissolved in 25 ml of methylene chloride are slowly added dropwise under argon. The mixture is stirred for a further 1.5 h while cooling in ice and is hydrolyzed with cold 2 N sodium hydroxide solution. The organic phase is separated off, and the aqueous phase is extracted 3 times more with methylene chloride. The combined organic phases are washed with saturated ammonium chloride solution, water and saturated sodium chloride solution and dried over sodium sulfate and the solvent is removed in vacuo. Crystallization of the residue in butyl acetate results in 7.60 g of solid product of melting point 148°–149° C.

C$_{11}$H$_{19}$N$_5$O$_3$S (301.38): calc.: C 43.84 H 6.35 N 23.24. found: C 43.7 H 6.4 N 21.1.

$^1$H NMR (60 MHz/DMSO): $\delta=8.23$ (d, J=6Hz, 1H); $\delta=6.75$ (d, J=6Hz, 1H); $\delta=4.82$ (t, J=5Hz, 1H); $\delta=3.73$ (m, 4H); $\delta=3.27$ (m, 4H); $\delta=2.78$ (s, 6H).

What is claimed is:

1. A pyrimidine derivative of the formula I

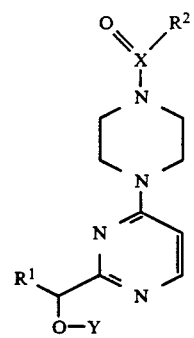

in which
R$^1$ is hydrogen
R$^2$ is C$_1$–C$_6$-alkyl, C$_5$–C$_7$-cycloalkyl, unsubstituted phenyl, phenyl which is mono- or disubstituted by methyl, chlorine, fluorine, trifluoromethyl, methoxy, CH$_3$—SO$_n$ with n equal to zero, 1 or 2, or —SO$_2$—NH$_2$, where in the case of disubstitution the substituents are identical or different,

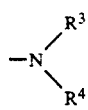

where $R^3$ and $R^4$ are identical or different and are hydrogen or $C_1$–$C_6$-alkyl, or is pyridyl or, if X is a carbon atom, is also hydrogen, X is a carbon atom or SO, and Y is hydrogen, $C_1$–$C_6$-alkyl, benzyl, acetyl or benzoyl, and the physiologically tolerated salts thereof.

2. A pyrimidine derivative as claimed in claim 1, wherein in formula I $R^1$ is hydrogen, $R^2$ is $C_1$–$C_3$-alkyl, unsubstituted phenyl or mono- or disubstituted phenyl, where the substituents have the stated meanings, and X and Y have the stated meanings 3. A pyrimidine derivative as claimed in claim 1, wherein in formula I $R^1$ is hydrogen, $R^2$ is

where $R^3$ and $R^4$ are identical or different and are methyl or ethyl,

X is SO and

Y has the stated meaning.

4. A pyrimidine derivative as claimed in claim 1, wherein in formula I $R^1$ is hydrogen $R^2$ is pyridyl, X is a carbon atom, and Y has the stated meaning.

5. A pyrimidine derivative as claimed in claim 1, wherein in formula I Y is a hydrogen atom.

6. A pyrimidine derivative of the formula I indicated in claim 1, in which $R^1$ is hydrogen, $R^2$ is

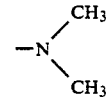

X is SO and Y is hydrogen, and the physiologically tolerated salts of this compound.

7. A method for causing a dose dependent increase in sorbitol concentration in a host which comprises
 administering to said host a compound as claimed in claim 1.

* * * * *

UNITED STATES PATENT AND TRADEMARK OFFICE
CERTIFICATE OF CORRECTION

PATENT NO. : 5,215,990
DATED : June 01, 1993
INVENTOR(S) : Dr. Karl Geisen et al.

It is certified that error appears in the above-indentified patent and that said Letters Patent is hereby corrected as shown below:

Claim 2, column 13, line 29, after "meanings" insert --.--.

Signed and Sealed this

Twenty-second Day of March, 1994

Attest:

BRUCE LEHMAN

*Attesting Officer*     *Commissioner of Patents and Trademarks*